(12) United States Patent
Condit et al.

(10) Patent No.: US 6,358,747 B1
(45) Date of Patent: Mar. 19, 2002

(54) METHOD AND APPARATUS FOR QUANTIFYING MOLYBDATE IN ABSORPTION REFRIGERATION SYSTEM BRINES

(75) Inventors: David A. Condit, Avon; Mark R. Jaworowski, Glastonbury; Xia Tang, West Hartford, all of CT (US)

(73) Assignee: Carrier Corporation, Farmington, CT (US)

( * ) Notice: Subject to any disclaimer, the term of this patent is extended or adjusted under 35 U.S.C. 154(b) by 0 days.

(21) Appl. No.: 09/324,376

(22) Filed: Jun. 2, 1999

(51) Int. Cl.$^7$ .............................................. G01N 33/20
(52) U.S. Cl. ............................ 436/83; 422/61; 436/73; 436/166
(58) Field of Search ........................... 436/73, 83, 166; 422/61

(56) References Cited

U.S. PATENT DOCUMENTS

| | | | |
|---|---|---|---|
| 5,106,581 A | * 4/1992 | Jaunakais et al. | 422/56 |
| 5,547,600 A | 8/1996 | Downey | 252/68 |
| 5,550,061 A | * 8/1996 | Stone | 436/73 |
| 5,744,365 A | * 4/1998 | Pellet et al. | 436/6 |

FOREIGN PATENT DOCUMENTS

JP      8-105835     * 4/1996

OTHER PUBLICATIONS

N. Gandolfo Gazz. Chim. Ital. 1945, 75, 62–70.*
I. Barshad Anal. Chem. 1949, 21, 1148–1150.*
T. D. Rees et al, Talanta 1968, 15, 1312–1314.*
D. S. Gaibakyan et al, J. Anal. Chem. 1970, 25, 2056–2059.*
Y. M. Dessouky et al, Analyst 1971, 96, 442–446.*
A. M. Kiememelj et al, Anal. Chem. 1976, 48, 575–578.*
H. Llambias et al, Chem. Abstr. 1978, 88, abstract 53021f.*
Lis et al., Journal of Alloys and Compounds 303–304, 132–136, 2000.*
Water Analysis Handbood, HACH Company, Loveland, Colorado, "Molybdenum, Molybdate", pp. 636.

* cited by examiner

Primary Examiner—Arlen Soderquist

(57) ABSTRACT

A method and apparatus are provided for quantifying molybdate corrosion inhibitor concentrations in lithium halide brines of absorption refrigeration systems. This permits monitoring and control of the inhibitor level. A reagent is chosen for reacting with the molybdate in the brine to provide a readily identifiable characteristic color, the intensity of which is a function and measure of the molybdate concentration. The reagent is an acidified reducing agent which reacts to provide a significant characteristic color capable of optical detection without interference. In a lithium bromide brine, the molybdate concentration is conveniently identified by reaction with stannous chloride SnCl in hydrochloric acid Hcl ($aq$). The resulting color corresponds to a wavelength of about 550–560 nm (pink), and the intensity is a function of molybdate concentration. Portable measuring equipment, such as a hand held spectrophotometer, or colorimeter, provide a convenient means for making on-site measurements.

5 Claims, 3 Drawing Sheets

METHOD AND APPARATUS FOR QUANTIFYING MOLYBDATE IN ABSORPTION REFRIGERATION SYSTEM BRINES

TECHNICAL FIELD

This invention relates generally to absorption refrigeration systems. More particularly, the invention relates to diagnostics for absorption refrigeration systems. More particularly still, the invention relates to a method and apparatus for performing diagnostics on a corrosion inhibitor present in absorption refrigeration systems.

BACKGROUND

There are a number of different pairs of refrigerants and absorbents that are used in absorption refrigeration systems. One such pair is water and a halogen salt of lithium, such as lithium bromide, lithium chloride or lithium iodide mixed to form a concentrated aqueous solution of the lithium salt. Another such pair is water and ammonia.

Iron and iron alloys like steel and copper and copper alloys are typical construction materials used in absorption refrigeration systems. Corrosion of these materials can cause difficulties. Not only is metal loss of concern but also the oxidation of ferrous metal can be accompanied by evolution of gaseous hydrogen. If not purged, the hydrogen can interfere with the proper operation of the system. Corrosion is of particular concern in systems that use halogen salts of lithium. And regardless of the refrigerant/absorbent pair used in a particular system, metal corrosion rates increase as system temperatures increase.

It is well known in the prior art that the addition of a salt of chromium, such as lithium chromate, to the refrigerant/absorbent solution in an absorption refrigeration system, is effective in reducing metallic corrosion. The presence of the chromate compound promotes the formation of a protective layer of iron and chromium oxides on the surfaces of the system that are in contact with the absorbent. With a decrease in iron oxidation, there is also a corresponding decrease in the production of noncondensible hydrogen. There is some concern, however, about the health risks that chromium presents. At least one government authority, the U.S. Environmental Protection Agency, has identified chromium as a carcinogen, and has prohibited the presence of chromium compounds in systems that are open to the atmosphere. Absorption refrigeration systems are, of course, closed systems, but a certain amount of working fluid from the system can become exposed to the atmosphere through the taking of samples, the manufacturing process and spills during handling and filling. And, at the end of the service life of a system, the system charge will necessarily require disposal of the working fluid, including the chromium compounds that it contains.

To address the foregoing concern, there has recently been developed a chromium-free aqueous solution, typically of a halogen salt of lithium, for use as a working fluid in an absorption refrigeration system. In addition, the solution also contains a compound containing a molybdate, a compound containing a borate and perhaps also, a compound containing a silicate. The added constituents act as effective corrosion inhibitors, with the inhibiting performance of the fluids being superior to lithium chromate inhibitors. This improved system of corrosion inhibitors is described in greater detail in U.S. Pat. No. 5,547,660 for *Absorption Refrigeration System working Fluid with Molybdate, Borate, Silicate Inhibitor Blend* by Downey and assigned to Carrier Corporation, which patent is incorporated herein by reference. Moreover, this improved system of corrosion inhibitors is employed in the WB-1 inhibited LiBr absorption chillers manufactured and sold by Carrier Corporation.

The aforementioned WB-1 inhibited LiBr absorption chiller of the Carrier Corporation uses an aqueous solution of water and a lithium halide, specifically lithium bromide (LiBr), as the working fluid (sometimes termed "brine"), and employ a further solution of lithium molybdate ($Li_2MoO_4$), lithium borate and lithium silicate as the corrosion inhibitor. Although the lithium borate and lithium silicate inhibitors remain in solution in the aqueous working fluid in adequate quantities throughout the life of the fluid system, the same may not be so with respect to the molybdate inhibitor. The lithium molybdate is only sparingly soluble in the LiBr brine, and must be maintained in the 100–200 ppm range to assure the desired action as a corrosion inhibitor. However, during start-up and/or during other times of stress on the refrigeration system, the molybdate inhibitor may become sufficiently depleted as to take it below the preferred concentration range and thus expose the system to corrosion problems.

To minimize the risk of corrosion problems which may result from an insufficient concentration of the molybdate inhibitor, it has been the practice to obtain samples of the LiBr brine in the field at the site of the absorption refrigeration system and to then send them to another location for analysis. That analysis is typically performed by a non-portable, relatively expensive technique and equipment, such as inductively coupled plasma-atomic emission spectroscopy (ICP-AES). This process occasions undesirable delays (measured in days) and significant monetary costs. Although various types of on-site analyzers and analysis techniques have been employed for monitoring the level of chromate inhibitor concentrations, including color comparators and spectrometers, those techniques as they presently exist are not suitable for determining molybdate concentrations. Similarly, existing analytical processes for determining concentrations of molybdate in refrigeration systems are operative if the working fluid is water, but not if it contains a lithium halide brine, such as lithium bromide.

Accordingly, there is a need for determining molybdate inhibitor concentrations in lithium halide brines using a method and/or apparatus which facilitates on-site analysis. The method and apparatus for making such on-site analysis should be relatively portable and economical, and provide rapid and accurate determination of molybdate inhibitor concentration.

SUMMARY OF THE INVENTION

The present invention provides a method and apparatus for making a rapid and accurate analysis of the concentration of molybdate inhibitor in a lithium halide brine at the site of a refrigeration system containing the brine. The analysis may be performed using relatively standard, portable equipment in a non-complex manner.

According to the invention, there is provided a method and apparatus for quantitatively analyzing molybdate inhibitor in a lithium halide brine, including lithium bromide and/or lithium chloride, typically at the site of a refrigeration system containing the brine. The system comprises reagent means and a means for determining molybdate concentration based on color analysis. The reagent means is mixed with a sample of the lithium halide brine having an unknown concentration of molybdate inhibitor, and is selected to create a characteristic color of the sample caused by the presence of the molybdate inhibitor, the intensity of that color also being a function of the concentration of molybdate inhibitor. The reagent means may be an acidified reducing agent or a separate acid and reducing agent, selected to produce a stable color change, and does so through a pH adjustment and a redox reaction. A spectrophotometer responsive to the optical wavelength of the characteristic color of the sample is a preferred means for indicating the presence of molybdate inhibitor in the brine sample. The spectrophotometer is also responsive to the intensity of that color to provide an indication of the concentration of the molybdate inhibitor in the sample. A color comparator provides an alternate means for determining the molybdate concentration.

In a representative refrigeration system in which the brine is lithium bromide, the selected reagent is stannous chloride $Sn(II)Cl_2$ in hydrochloric acid HCl ($aq$), and the resulting characteristic color of the sample containing the molybdate inhibitor absorbs visible light in the range of 520–580 nm, and more particularly is a pink color which absorbs visible light with a maximum near about 550–560 nm. The spectrophotometer may be a hand-held colorimeter operative only near about 550 nm.

The process of the invention includes obtaining a sample of the lithium halide brine containing the unknown quantity of molybdate inhibitor, mixing a selected reagent with that sample to provide a characteristic color, analyzing the sample to determine the presence and optical intensity of that characteristic color, and providing an indication of the concentration of molybdate inhibitor in the brine sample as a function of the determined presence and intensity of the characteristic color.

The analysis of the sample is conducted spectrophotometrically, preferably using a portable spectrophotometer or colorimeter responsive to the optical wavelength of the characteristic color. The spectrophotometer is field calibrated using a brine sample having a known concentration of molybdate inhibitor, typically zero, to establish a reference. For a lithium bromide brine, the selected reagent is stannous chloride in hydrochloric acid, and the resulting characteristic color corresponds to a wavelength in the range of 520–580 nm, typically pink with a maximum near 550–560 nm.

BEST MODE FOR CARRYING OUT THE INVENTION

Figure 1:
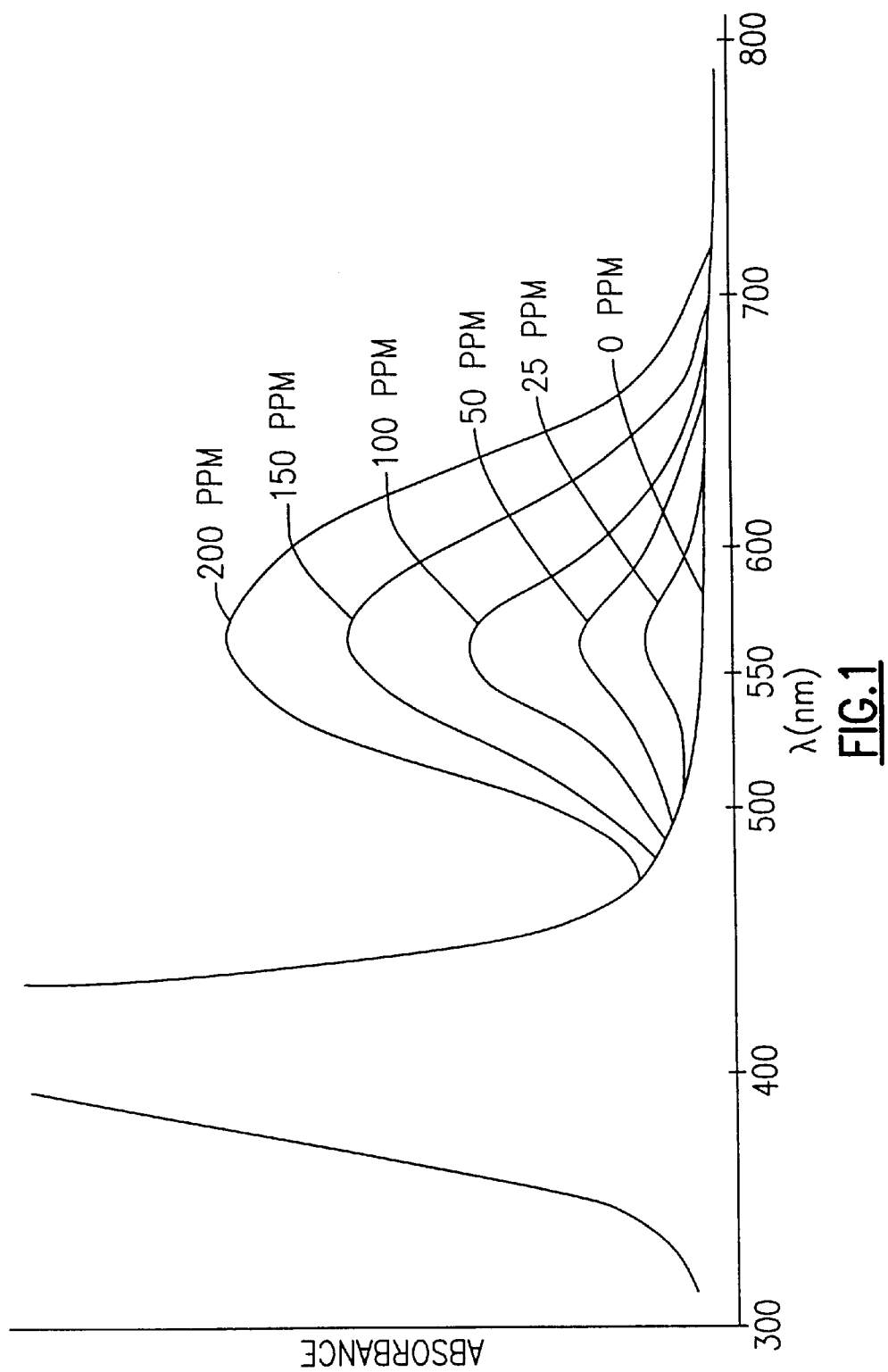
FIG. 1 is a spectral plot of the absorbance spectrum of a lithium bromide brine, treated with a reagent, for differing concentrations of included lithium molybdate inhibitor.

The present invention recognizes that a particular reagent, when mixed with a lithium halide brine, particularly lithium bromide, containing a lithium molybdate corrosion inhibitor, will provide a particular colorimetric response which is accurately indicative of the concentration of the molybdate inhibitor. This recognition is extended and applied to the utilization of portable, economical diagnostic equipment for making on-site determinations of molybdate inhibitor concentrations in absorption refrigeration systems.

In accordance with the invention, a representative refrigeration system (not shown) employs an aqueous solution of water and a lithium halide, typically lithium bromide LiBr, as the working fluid, or brine, in the absorption chiller. In some instances, LiCl may be the halide of lithium. The concentration of LiBr in the brines is typically in the range of 50–60%, and in the present embodiment about 55%. The refrigeration system further employs a solution of lithium molybdate $Li_2MoO_4$, lithium borate and lithium silicate as the corrosion inhibitor. The lithium molybdate is only sparingly soluble in the LiBr brine and must be maintained in the 100–200 ppm range to assure the desired function as a corrosion inhibitor.

To monitor the level or concentration of lithium molybdate inhibitor in a rapid, accurate and convenient manner at the site of the refrigeration system, a system and method have been developed which permit the use of portable, handheld analytical instruments to provide such measurements. It has been discovered that a reagent which is an acidified reducing agent, when mixed and reacted with a sample of LiBr brine having a molybdate inhibitor present in an unknown concentration, will create a characteristic color in the mix which indicates, by its presence and optical intensity, the presence and concentration of molybdate inhibitor. A suitable portable spectrophotometric instrument or other device is then used to make the quantitative determinations. The reagent is chosen to provide the characteristic color without interfering with the optical detection of the characteristic color.

A one-step acidification and reduction reaction uses, as a reagent, stannous chloride $SnCl_2$ in hydrochloric acid HCl ($aq$), to reduce molybdenum and form a pink color in the visible spectrum range between about 520 and 580 nm (nanometers). More specifically, the particular reaction is believed to involve the reduction of Mo(VI) ($Li_2MoO_4$) to Mo(III) under acidic conditions. The resulting complex is believed to be $[MoX_6]^{3-}$ or $[MoX_5(H_2O)]^{2-}$ where $X=Br^-$ or or $Cl^-$. Those complexes typically possess a characteristic color of red, or more accurately pink, in the 550–560 nm range of the visible spectrum. The reaction occurs at room temperature and reaches completion within 10 minutes. Moreover, the developed color remains stable for at least 48 hours at room temperature, provided the reducing agent, $SnCl_2$ or $SnBr_2$ has not been depleted. Importantly, soluble copper, a common contaminant in used brine, does not interfere at concentrations up to about 500 ppm. The concentrations of copper in used brine are typically less than 500 ppm. Similarly, no other contaminants in used brines were found to interfere with the desirable characteristics of this particular reagent and its reaction with molybdates.

Reference is made to FIG. 1, which depicts the (optical) absorbance of the LiBr brine and the included lithium molybdate, lithium borate and lithium silicate inhibitors of the WB-1 inhibitor complex that has been treated with the reagent. Particular notice should be taken of the absorbance do to the reduced molybdenum complex in the general region of 500–600 nm. More specifically, in the region from about 520 to 580 nm, the intensity of the absorbance is seen to be significantly elevated as a function of the concentration of the molybdate inhibitor. The maximum absorbance occasioned by the presence of molybdate appears in the region of about 550 to 560 nm, and is characterized as a pink color.

Referring further to FIG. 1 in the spectral region between about 500 and 600 nm, there is depicted the absorbance of the LiBr brine for various concentrations of lithium molybdate inhibitor reacted with the $SnCl_2$ in HCl (aq). The concentrations of molybdate range from 0 ppm to 200 ppm, as indicated on the several spectral scans in that region. It will be noted that the presence of molybdate is readily discernible, even in relatively small concentrations, by the characteristic rise in the absorbance in the region of 520 to 580 nm, and particularly at the maximum region of about 550 to 560 nm. Also important is the generally linear relationship existing between the concentration of molybdate and the optical absorption characteristic at is the wavelength region of interest. In FIG. 1, the absorbencies for molybdate concentrations of 0, 25, 50, 100, 150 and 200 ppm are depicted, thus covering the range of interest for concentrations of molybdate dissolved in the LiBr brine.

Figure 2:
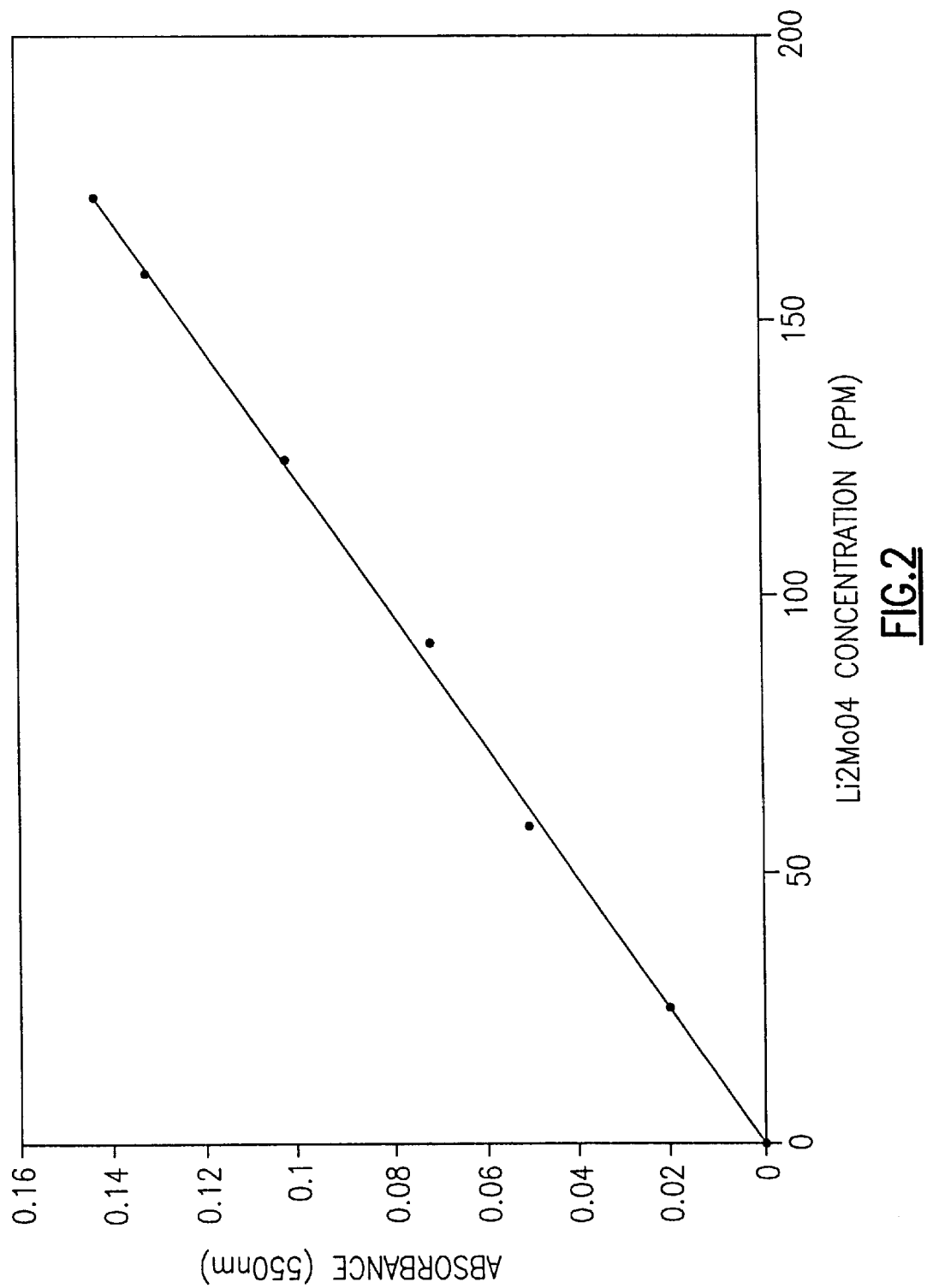
FIG. 2 is a graphical plot of the spectral absorbance at 550 nm for different concentrations of lithium molybdate in lithium bromide brine, showing the generally linear relationship.

Referring to FIG. 2, there is graphically depicted the optical absorbance characteristic for the reacted molybdate at about 550 nm as a function of the molybdate concentration in the 55% LiBr brine. This emphasizes the general linearity of the relationship, thus facilitating the use of absorption spectroscopy, and particularly spectrophotometers or calorimeters adapted for use at or near the 550 to 560 nm wavelength range. Moreover, the slope or sensitivity of the relationship is great enough to provide adequate discrimination to a measuring instrument. The absorbance characteristic of FIG. 2 was depicted at 550 nm, which is a convenient, commercially available system. However, the peak response is closer to 560 nm, and a steeper slope is possible at that wavelength if increased sensitivity is required.

Figure 3:
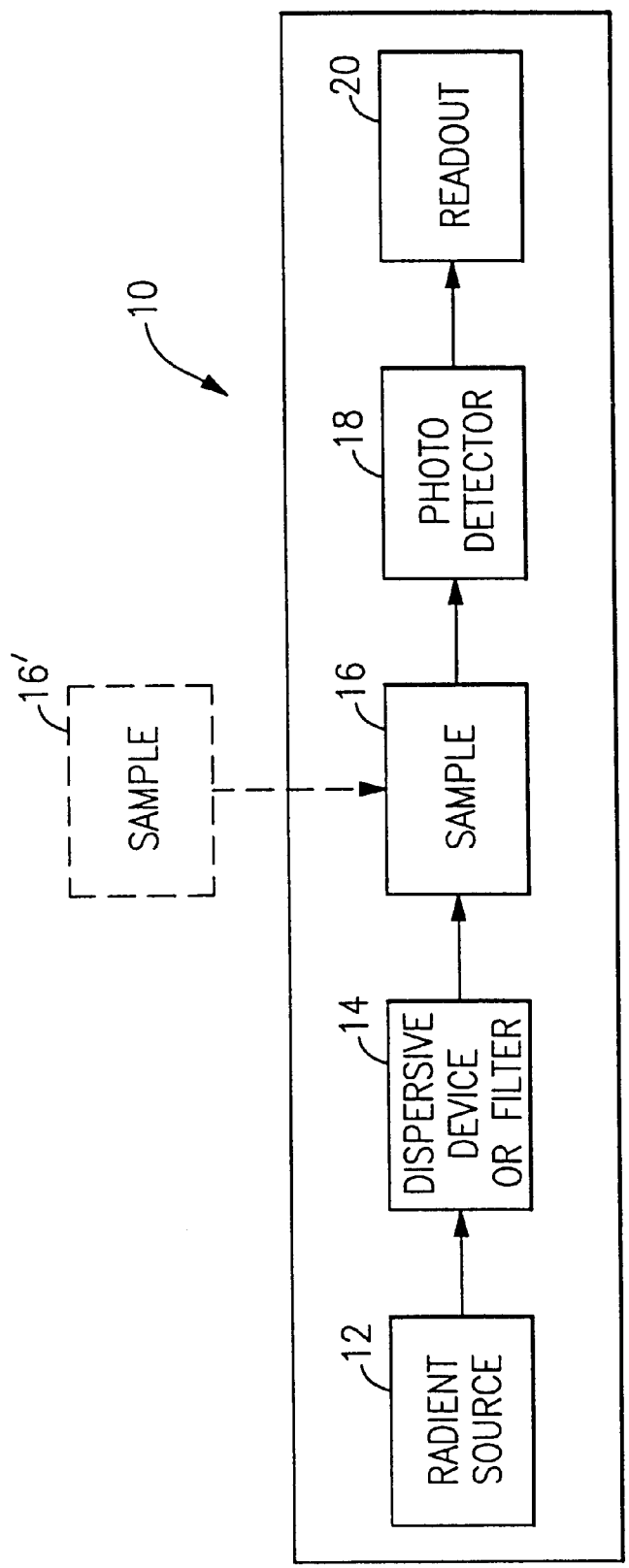
FIG. 3 is a generalized functional block diagram of a spectrophotometer for use in the analytical system and process of the invention.

Referring to FIG. 3, there is depicted, in block diagram form, a spectrophotometric instrument capable of making the analytical measurements of the present invention. The spectrophotometric instrument, typically a spectrophotometer or colorimeter 10, includes a radiation source 12; a dispersive device or a filter 14; a sample holder, or cell, 16; a detector 18, such as a photo detector and amplifier; and a readout system 20. The sample 16, as represented in broken line 16', may be prepared separately and subsequently inserted into the spectrophotometer 10.

In accordance with the invention, the spectrophotometer 10 is preferably and typically portable, and may be hand-held during use on-site. The HACH Generic Pocket Portable Colorimeter, manufactured and sold by HACH Company of Loveland, Colo. is relatively small and portable, thus being readily useable for on-site analysis of molybdate concentrations in absorption refrigeration systems. Moreover, the HACH calorimeter 10 affords the accuracy and economy required or desired of such an instrument. The colorimeter 10 is selected to be responsive substantially only in the optical range of interest, in this instance about 550 or 560 nm wavelength. The colorimeter 10 used herein was responsive at the 550 nm wavelength.

In use, the analytical process of the invention was practiced using the HACH Portable Colorimeter 10 according to the following procedure. The colorimeter 10 is precalibrated for the measurement of molybdate concentrations in 50–60% LiBr brines having the WB-1 corrosion inhibitors (lithium molybdate, lithium borate and lithium silicate). This precalibration incorporates the slope of the relationship depicted in FIG. 2. The reagent for reacting with the molybdate inhibitor is 0.3M $SnCl_2$ in 6N HCl (aq). A further sample of uninhibited (no corrosion inhibitor) LiBr brine (50% or above) is also provided as a reference sample (blank). The field calibration procedure includes the following steps:

Use a 5 or 10 mL syringe to measure 10 mL of uninhibited LiBr brine into a sample bottle (cell). Name this solution as "blank."

Use a 5 or 10 mL syringe, with a 1.0 μm filter attached, to deliver 10 mL of each sample solution of "unknown" molybdate concentration into a separate cell. The filter removes particulate to provide a clear solution.

Add 1 mL of molybdate reagent into the cells containing blank and unknown sample solutions.

Cap each cell tightly and mix.

Wait for 10 min to allow the color to fully develop.

Insert the cell containing blank solution (uninhibited LiBr) into the sample cell compartment of the HACH colorimeter with the diamond mark facing the keyboard.

Cover the cell with the instrument cap. Orient the cap's curved surface toward the keyboard to match the grooves in the instrument case.

Zero the instrument by pressing the ZERO key.

Measure $Li_2MoO_4$ concentration in each unknown sample by inserting the unknown sample cell, covering the cell compartment and pressing the READ key.

Multiply the number displayed in the instrument readout by 100 to obtain $Li_2MoO_4$ concentration in PPM.

The $Li_2MoO_4$ concentration measured using this method is not normalized to 55% LiBr.

Tests comparing the above-described equipment and process with the more is conventional, standard ICP process yield results which demonstrate the accuracy and repeatability of the technique. The range of variation between the techniques is acceptable in monitoring the concentrations of molybdate inhibitor in the chiller brines to assure that concentrations in the 100–200 ppm range can be maintained.

The preferred embodiment has described the use of a colorimeter 10 for determining the concentration of molybdate in a sample, to obtain the accuracy, objectivity, and repeatability of such an instrument in making colorimetric determinations. However, it will be appreciated that other means may be used for determining molybdate concentration based on the intensity of the characteristic color of the reacted sample. For instance, another technique which may be used for on-site analysis comprises the use of a color comparator system in which the user is provided with an array of reference color indicia or charts correlated to respective concentrations of molybdate in the reacted sample. By visually comparing the color of the reacted sample to the reference color indicia, the user can determine the closest color match and an associated value of molybdate concentration. This technique is inexpensive but typically less objective and accurate than the colorimeter.

Although the invention has been described and illustrated with respect to the exemplary embodiments thereof, it should be understood by those skilled in the art that the foregoing and various other changes, omissions and additions may be made without departing from the spirit and scope of the invention.

What is claimed:

1. A method of quantitatively analyzing molybdate inhibitor present in lithium bromide brine, comprising the steps of:

obtaining a sample of the lithium bromide brine containing an unknown quantity of molybdate inhibitor;

mixing a selected reagent which consists of $SnCl_2$ in HCl (aq) with the sample to create a characteristic color of the sample in the presence of molybdate inhibitor, the intensity of the characteristic color being a function of the concentration of molybdate inhibitor and corresponding to a wavelength in the range of about 520–580 nm;

analyzing the sample to determine the presence and the intensity of the characteristic color; and providing an indication of the concentration of molybdate inhibitor in the lithium bromide brine of the sample as a function of the presence and intensity of the characteristic color.

2. The method of claim 1 wherein the sample is analyzed and an indication of molybdate concentration is provided using a spectrophotometer, and further comprising the step of calibrating the spectrophotometer.

3. The method of claim 2, wherein the step of spectrophotometrically analyzing the sample containing molybdate inhibitor is performed on a hand-held colorimeter.

4. The method of claim 1 wherein the step of obtaining a sample of lithium bromide brine containing an unknown quantity of molybdate inhibitor further includes the step of filtering said sample to remove suspended particulate.

5. The method of claim 1 wherein the sample is analyzed and an indication of molybdate concentration is provided by a user of a color comparator system, the user determining molybdate concentration by comparing the characteristic color and intensity of the sample with color references correlated with and indicating differing molybdate concentrations.

* * * * *